US005830846A

United States Patent [19]

Bertram et al.

[11] Patent Number: 5,830,846

[45] Date of Patent: Nov. 3, 1998

[54] USE OF 3-ACYLTHIOHEXYL ESTERS AS AROMA AND ODORIFEROUS SUBSTANCES

[75] Inventors: Heinz-Jürgen Bertram; Jürgen Brüning; Matthias Güntert, all of Holzminden; Peter Werkhoff, Höxter; Peter Wörner, Holzminden, all of Germany

[73] Assignee: Haarmann & Reimer GmbH, Holzminden, Germany

[21] Appl. No.: 916,485

[22] Filed: Aug. 22, 1997

[30] Foreign Application Priority Data

Aug. 27, 1996 [DE] Germany ........................ 196 34 520.0

[51] Int. Cl.$^6$ ........................ A61K 7/46

[52] U.S. Cl. ........................ 512/7; 558/255; 426/650

[58] Field of Search ........................ 512/7; 558/225; 426/650

[56] References Cited

U.S. PATENT DOCUMENTS 2,423,641 7/1947 Elingboe ........................ 558/255

OTHER PUBLICATIONS

Heusinger et al, Tetrahedron Letters, vol. 25, p. 507, 1984.

Engel et al, J. Agric. Food Chem., vol. 39, p. 2251, 1991.

K–H. Engel, et al., Identification of New Sulfur–Containing Volatiles in Yellow Passion Fruits (*Passiflora edulis f. flavicarpa*), J. Agric. Food Chem., vol. 39, No. 12, pp. 2249–2252, (1991).

G. Heusinger, et al., Chirale, Schwefelhaltige Aromastoffe der Gelben Passionsfrucht (*Passiflora edulis f. flavicarpa*) Darstellung der Enantiomeren und Absolute Konfiguration, Tetrahedron Letters, vol. 25, No. 5, pp. 507–510, (1984).

*Primary Examiner*—James H. Reamer

*Attorney, Agent, or Firm*—Sprung Kramer Schaefer & Briscoe

[57] ABSTRACT

Use of 3-acylthiohexyl esters of the formula

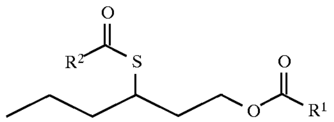

wherein $R^1$ and $R^2$ independently of one another represent hydrogen, $C_1$–$C_6$-alkyl or $C_5$–$C_{12}$-aryl, including furyl and thienyl, as aroma and/or odoriferous substances, and aroma and odoriferous substance compositions containing these compounds.

4 Claims, No Drawings

USE OF 3-ACYLTHIOHEXYL ESTERS AS AROMA AND ODORIFEROUS SUBSTANCES

The invention relates to the use of 3-acylthiohexyl esters of the formula (I)

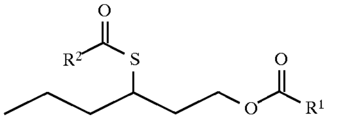

wherein $R^1$ and $R^2$ independently of one another represent hydrogen, $C_1$–$C_6$-alkyl or $C_5$–$C_{12}$-aryl, including furyl and thienyl, as aroma substances and/or odoriferous substances, and to aroma and odoriferous substance compositions comprising these compounds.

Although 3-acylthiohexyl esters have been described individually in the literature, the sensorial relevance of these compounds has not hitherto been recognized. Thus, 3-acryloylthiohexyl acetate is obtained as a by-product in the synthesis of 3-mercaptohexyl acetate (G. Heusinger and A. Mosandl in Tetrahedron Letters 25, 507, 1984 and K.-H. Engel and R. Tressl in J. Agric. Food Chem. 39, 2251, 1991), 3-(2-methyl-2-phenylthio) hexyl acetate has been prepare as an intermediate product (G. Heusinger and A. Mosandl in Tetrahedron Letters 25, 507, 1984), and 3-butanoylthiohexyl acetate has been obtained as an intermediate product in the preparation of 3-mercaptohexyl butyrate. 3-Acetylthiohexyl acetate, 3-butanoylthiohexyl butanoate and 3-hexanoylthiohexyl hexanoate have furthermore been described as by-products in syntheses (K.-H. Engel and R. Tressl in J. Agric. Food Chem. 39, 2251, 1991).

However, statements on the properties of these compounds in terms of smell and flavour have not been made in any of the cases. Statements on the physical properties are to be found only for 3-acetylthiohexyl acetate. This is described as "readily volatile and removable with the solvent" (G. Heusinger and A. Mosandl in Tetrahedron Letters 25, 507, 1984).

It has now been found, surprisingly, that the 3-acylthiohexyl esters of the formula I have interesting organoleptic properties which render them valuable aroma and odoriferous substances. The compounds have a considerably better adhesion and stability here than the corresponding free thiols and are distinguished by an intensive smell and flavour of tropical fruits.

The compounds I according to the invention can be employed here both as a racemic mixture and in an enantioselectively concentrated or in an optically pure form.

3-Propionylthiohexyl propionate, 3-acetylthiohexyl propionate, 3-propionylthiohexyl acetate and 3-acetylthiohexyl acetate are particularly preferred.

In addition to the specific classification in the direction of tropical fruit, the compounds are particularly suitable for intensifying the fullness and having a rounding-off action in fruit aroma compositions.

The aroma compositions prepared using the compounds to be used according to the invention can be employed in the entire foodstuffs and luxury goods sector. They are particularly suitable for fruit formulations, fatty compositions, baked goods, yoghurt, ice cream, confectionery and fruit juice formulations.

The 3-acylthiohexyl esters to be used according to the invention can be employed in amounts of 1 ppb to 1% by weight, preferably 5 ppb to 50% by weight, based on the ready-to-eat foodstuff.

On the basis of their good adhesion and their good stability, the compounds to be used according to the invention furthermore are outstandingly suitable for use in odoriferous compositions.

The 3-acylthiohexyl esters to be used according to the invention have an advantageous effect in a wide range of fragrance notes, for example those of the blossomy-fruity type. They can be employed for the entire range of perfuming. As well as in fine perfumery, such compositions are employed in particular for perfuming cosmetics, such as creams, lotions, aerosols, toilet soaps, industrial perfumery articles (air fresheners, diesel, benzine, heating oil, polyurethane foam, latex, PVC, insecticides), softeners, detergents, disinfectants and textile treatment compositions.

The 3-acylthiohexyl esters I to be used according to the invention can be prepared, for example, by esterification of 3-mercaptohexanol (II)

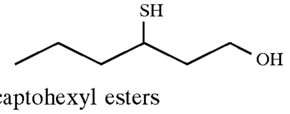

or of 3-mercaptohexyl esters (III)

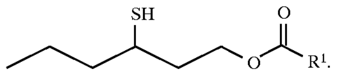

One-stage esterification of 3-mercaptohexanol is suitable above all for the cases where two identical acyl radicals are desired. Two-stage synthesis from 3-mercaptohexanol via the 3-mercaptohexyl ester as an intermediate stage is preferably chosen if two different acyl radicals are desired; in this case, the hydroxyl group is first esterified, if appropriate the resulting ester is freed from by-products, and the mercapto group is then esterified.

Suitable carboxylic acid derivatives for the esterification are, above all, acid chlorides and anhydrides; the amounts are preferably 1 to 3 mol per mol of OH or SH of the component to be esterified. If acid chlorides are used, bases, such as, for example, triethylamine, dimethylbenzylamine or pyridine, can be added as acid-trapping agents. The esterifications can take place in the presence or absence of organic solvents; preferred solvents include, for example, ethers, such as diethyl and dibutyl ether, aromatics, such as toluene and xylene, and halogenoaromatics, such as chlorobenzene. Preferred reaction temperatures are in the range from 50° to 150° C. The reaction mixtures can be worked up by customary methods.

EXAMPLES

A. Preparation

Preparation of 3-propionylthiohexyl propionate 1.2 mol of propionic anhydride are initially introduced into the reaction vessel and are heated up to 90° C. 0.5 mol of 3-mercaptohexanol is then metered in and the mixture is heated at 140° C. for a further 2 hours. It is allowed to cool to 50° C., 50 ml of methanol are added and the mixture is stirred at this temperature for 1 hour. Methanol and methyl propionate are then first distilled off as first runnings, in order then to distill the 3-propionylthiohexyl propionate in vacuo, boiling point (2.2 mbar): 113° C.

The following compounds, for example, can be prepared analogously to this process:

3-Acetylthiohexyl acetate

3-Acetylthiohexyl propionate

3-Acetylthiohexyl butyrate

3-Propionylthiohexyl acetate

3-Butyrylthiohexyl acetate

3-Butyrylthiohexyl butyrate

3-Acetylthiohexyl caproate

3-Hexylthiohexyl acetate

3-Hexylthiohexyl caproate

3-Isobutyrylthiohexyl acetate

3-Acetylthiohexyl isobutyrate

3-Isobutyrylthiohexyl isobutyrate

B. Sensorial analysis

Flavour descriptions determined by a test panel of 6 specially trained testers for some of the compounds I when used in 0.5% strength by weight aqueous sugar solution are:

3-Acetylthiohexyl acetate
when added in an amount of 100 ppb: tropical, fruity, passion fruit, fullness 3-Propionylthiohexyl propionate
when added in an amount of 100 ppb: tropical, fruity, passion fruit, fullness 3-Acetylthiohexyl butyrate
when added in an amount of 500 ppb: tropical, sweet, fruity 3-Acetylthiohexyl caproate
when added in an amount of 500 ppb: tropical, passion fruit, adheres C. Use Use Example 1

A fruit aroma composition is prepared by mixing the following constituents:

| | Parts by weight |
|---|---|
| Propylene glycol | 490 |
| Ethyl butyrate | 200 |
| Ethyl caproate | 100 |
| Hexyl caproate | 75 |
| Hexyl butyrate | 50 |
| Hexanol | 40 |
| 3Z-Hexenol | 20 |
| Caproic acid | 10 |
| Linalool | 5 |
| Benzyl acetate | 5 |
| Benzaldehyde | 2 |
| Damascenone | 1 |
| α-Damascone | 1 |
| γ-Decalactone | 1 |
| | 1000 |

By addition of 1–10 parts by weight of 3-propionylthiohexyl propionate, the aroma acquires a significant intensification of flavour in the direction of tropical fruit.

Use Example 2

A perfume composition is prepared by mixing the following components:

| | Parts by weight |
|---|---|
| 2-Phenoxyethyl i-butyrate | 200 |
| Terpineol | 150 |
| Linalool | 150 |
| alpha-Amylcinnamaldehyde | 100 |
| Orange oil | 100 |
| Triethyl citrate | 65 |
| Citronellyl acetate | 50 |
| Hexyl salicylate | 50 |
| Bergamot oil | 30 |
| Ylang ylang oil | 25 |
| Ambrosia | 25 |
| Citral | 20 |
| Lilial | 10 |
| Pyroprunate | 10 |
| Aldehyde C16, so-called | 5 |
| Mandarin oil | 5 |
| Allylionone | 2 |
| Vertocitral | 2 |
| Farenal | 1 |
| | 1000 |

By addition of 1–10 parts by weight of 3-propionylthiohexyl propionate, the composition acquires a significant intensification of smell in the direction of tropical fruit.

D. Physical values of some compounds

| | $n_D^{20}$ | bp (°C./mbar) |
|---|---|---|
| 3-Acetylthiohexyl acetate | 1.4677 | 90/4 |
| 3-Propionylthiohexyl propionate | 1.4660 | 113/2.2 |
| 3-Acetylthiohexyl butyrate | 1.4651 | 111/4 |
| 3-Acetylthiohexyl caproate | 1.4656 | 120/0.7 |

E. IR spectra of some compounds

| Wave number | Intensity |
|---|---|
| **3-Acetylthiohexyl acetate** | |
| 2959 | m |
| 2933 | m |
| 1737 | s |
| 1689 | s |
| 1426 | w |
| 1366 | m |
| 1250 | s |
| 1112 | m |
| 1038 | m |
| 957 | w |
| **3-Butyrylthiohexyl acetate** | |
| 2962 | m |
| 2934 | m |
| 1738 | s |
| 1689 | s |
| 1467 | w |
| 1366 | w |
| 1250 | s |
| 1116 | m |
| 1038 | m |
| 990 | w |
| **3-Acetylthiohexyl butyrate** | |
| 2959 | m |
| 2933 | m |
| 1736 | s |
| 1689 | s |
| 1429 | w |
| 1366 | m |
| 1250 | s |
| 1112 | m |
| 1037 | m |
| 958 | w |
| **3-Propionylthiohexyl acetate** | |
| 2958 | m |
| 2936 | m |
| 1737 | s |
| 1691 | s |

-continued

| Wave number | Intensity |
|---|---|
| 1460 | w |
| 1366 | m |
| 1250 | s |
| 1091 | m |
| 1036 | m |
| 939 | s |
| 3-Acetylthiohexyl propionate | |
| 2958 | m |
| 2935 | m |
| 1736 | s |
| 1690 | s |
| 1464 | w |
| 1355 | m |
| 1187 | s |
| 1111 | m |
| 1036 | w |
| 960 | w |
| 3-Propionylthiohexyl propionate | |
| 2958 | m |
| 2939 | m |
| 2874 | m |
| 1737 | s |
| 1693 | s |
| 1462 | w |
| 1186 | m |
| 1088 | w |
| 1021 | w |
| 939 | m |
| 3-Butyrylthiohexyl butyrate | |
| 2961 | s |
| 2933 | m |
| 2873 | m |
| 1734 | s |
| 1688 | s |
| 1465 | m |
| 1362 | m |
| 1180 | s |
| 1114 | m |
| 989 | m |
| 3-Isobutyrylthiohexyl acetate | |
| 861 | m |
| 977 | m |
| 1037 | m |
| 1250 | s |
| 1365 | m |
| 1468 | m |
| 1688 | s |
| 1738 | s |
| 2934 | m |
| 2966 | m |
| 3-Acetylthiohexyl isobutyrate | |
| 1114 | m |
| 1161 | s |
| 1196 | m |
| 1353 | m |
| 1469 | m |
| 1690 | s |
| 1732 | s |
| 2874 | m |
| 2934 | m |
| 2961 | m |
| 3-Isobutyrylthiohexyl isobutyrate | |
| 861 | m |
| 976 | m |
| 1160 | m |
| 1193 | m |
| 1468 | m |
| 1689 | s |
| 1734 | s |
| 2874 | m |
| 2934 | m |
| 2970 | m |

(w = weak, m = moderate, s = strong)

We claim:

1. An aroma or odoriferous composition comprising a compound of the formula

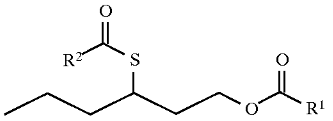

(I)

wherein $R^1$ and $R^2$ independently of one another represent hydrogen, $C_1$–$C_6$-alkyl or $C_5$–$C_{12}$-aryl.

2. 3-Propionylthiohexyl propionate.

3. A method of enhancing the aroma of a foodstuff which comprises adding to such foodstuff from 1 ppb to 1% by weight of the compound (I) according to claim 1.

4. A method of perfuming cosmetics which comprises adding to such cosmetics a compound of formula (I) according to claim 1.

* * * * *